(12) United States Patent
Hoernig

(10) Patent No.: US 10,028,708 B2
(45) Date of Patent: Jul. 24, 2018

(54) METHOD FOR RECORDING A TOMOSYNTHESIS DATA SET WITH AN X-RAY DEVICE, AND X-RAY DEVICE

(71) Applicant: SIEMENS AKTIENGESELLSCHAFT, Munich (DE)

(72) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 226 days.

(21) Appl. No.: 14/992,189

(22) Filed: Jan. 11, 2016

(65) Prior Publication Data

US 2016/0199010 A1 Jul. 14, 2016

(30) Foreign Application Priority Data

Jan. 9, 2015 (DE) .................. 10 2015 200 180

(51) Int. Cl.
| | |
|---|---|
| *A61B 6/04* | (2006.01) |
| *A61B 6/02* | (2006.01) |
| *A61B 6/00* | (2006.01) |
| A61B 6/08 | (2006.01) |

(52) U.S. Cl.
CPC ............... *A61B 6/025* (2013.01); *A61B 6/04* (2013.01); *A61B 6/0414* (2013.01); *A61B 6/4435* (2013.01); *A61B 6/4441* (2013.01); *A61B 6/4482* (2013.01); *A61B 6/488* (2013.01); *A61B 6/502* (2013.01); *A61B 6/5217* (2013.01); *A61B 6/544* (2013.01); *A61B 6/545* (2013.01); *A61B 6/08* (2013.01); *A61B 6/469* (2013.01); *A61B 6/5205* (2013.01)

(58) Field of Classification Search
CPC ......... A61B 6/032; A61B 6/502; A61B 6/025; A61B 6/463; A61B 8/4416; A61B 2090/3908; A61B 6/0414; A61B 6/482
USPC ................................................. 378/37
See application file for complete search history.

(56) References Cited

U.S. PATENT DOCUMENTS

| | | | |
|---|---|---|---|
| 9,020,094 | B2 | 4/2015 | Popova et al. |
| 2012/0051500 | A1 | 3/2012 | Johansson et al. |
| 2012/0140878 | A1 | 6/2012 | Souchay |

(Continued)

FOREIGN PATENT DOCUMENTS

| | | |
|---|---|---|
| DE | 202009018884 U1 | 4/2012 |
| DE | 102011057133 A1 | 7/2012 |
| FR | 2881338 A1 | 8/2006 |

*Primary Examiner* — Don Wong
(74) *Attorney, Agent, or Firm* — Laurence Greenberg; Werner Stemer; Ralph Locher

(57) ABSTRACT

A method records a tomosynthesis data set of a breast of a patient with an X-ray device. The device contains an X-ray detector for the support of the breast, a compression plate for the breast and being parallel to the X-ray detector, and an X-ray source, which is movable in a basic angle interval around a central position, in which the midperpendicular of the detector area corresponds to the central ray of the X-ray source. The tomosynthesis data set is reconstructed from projection images recorded at different projection angles over a recording interval. A recording angle interval that is asymmetrical relative to the central position is used in the case of an asymmetrically positioned breast, in particular for an MLO view.

15 Claims, 4 Drawing Sheets

(56) References Cited

U.S. PATENT DOCUMENTS

2015/0036796 A1* 2/2015 Dornberger .......... A61B 6/0414
378/37
2016/0256125 A1* 9/2016 Smith .................... A61B 6/025

* cited by examiner

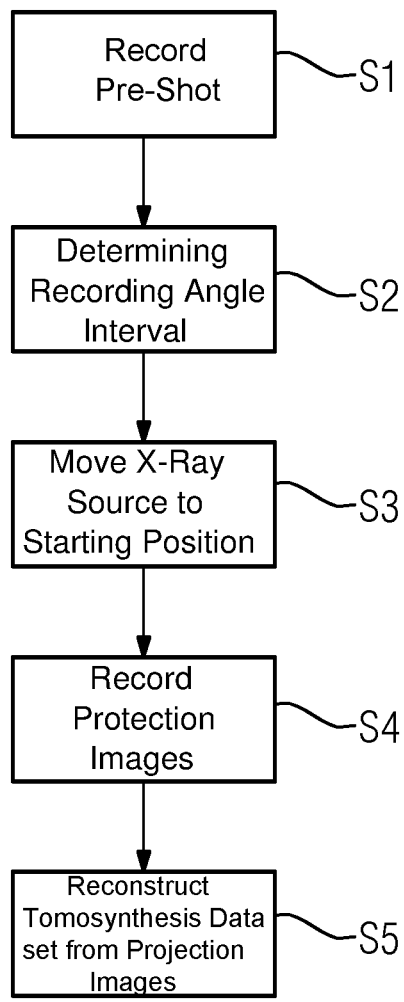

METHOD FOR RECORDING A TOMOSYNTHESIS DATA SET WITH AN X-RAY DEVICE, AND X-RAY DEVICE

CROSS-REFERENCE TO RELATED APPLICATION

This application claims the priority, under 35 U.S.C. § 119, of German application DE 10 2015 200 180.6, filed Jan. 9, 2015; the prior application is herewith incorporated by reference in its entirety.

BACKGROUND OF THE INVENTION

Field of the Invention

The invention relates to a method for recording a tomosynthesis data set of a breast of a patient with an X-ray device containing an X-ray detector for the support of the breast, a compression plate and an X-ray source, which is movable in a basic angle interval around a central position, in which the midperpendicular of the detector area corresponds to the central ray of the X-ray source, for the purpose of recording projection images at different projection angles into different angular positions. The tomosynthesis data set is reconstructed from projection images recorded at different projection angles over a recording interval. Moreover, the invention relates to an X-ray device.

Three-dimensional tomosynthesis of the female breast (Mamma) is already conventional practice as a diagnostic method in the prior art. This involves using an X-ray device which, as known in principle, contains an X-ray source and an X-ray detector. The breast to be examined can be placed onto the X-ray detector, wherein use is made of a compression by a compression plate provided above the X-ray detector, the compression plate running parallel to the X-ray detector and being displaceable perpendicular to the detector area and being transmissive to X-ray radiation. The central position (also called basic position) of the X-ray source is in this case the position in which the central ray thereof corresponds to the midperpendicular of the detector area of the X-ray detector; according to general convention, the associated projection angle is defined as 0°. The X-ray source is arranged such that it is pivotable by a pivoting device, with the result that, with the detector stationary, projection images can be recorded from different projection angles. Recording angle intervals having a length of between 15° and 50° are usually used here, wherein the maximum pivoting of the X-ray source relative to the X-ray detector is chosen to be of the same magnitude in both directions; consequently, a multiplicity of projection images are recorded for example symmetrically around the central position, for example from −25° to +25°. By use of conventional, known reconstruction methods, a three-dimensional tomosynthesis data set, for example as slice images succeeding one another in a direction perpendicular to the detector area of the X-ray detector, can be reconstructed from the projection images from different projection directions.

Two fundamental recording variants are known in this case. The first of these is the so-called cranial-caudal (CC) view, in the case of which the breast is positioned centrally on the X-ray detector with the latter usually arranged horizontally, such that the central ray usually runs horizontally in the central position. In addition to the CC view, an MLO view is frequently recorded, too, where MLO stands for "mediolateral oblique". For this purpose, the entire recording arrangement containing a detector with compression plate and X-ray source is tilted by a specific angle, for example by 45°, in some cases even by 60°, wherein the patient's arm usually rests on a mount for the X-ray detector, such that the breast projects laterally into the interspace between the compression plate and the X-ray detector. In this case, a distinction is drawn between RMLO (right-hand side) and LMLO (left-hand side). Other views are also conceivable in which the breast is positioned asymmetrically (for example generally mediolateral views).

In contrast to the CC view, therefore the breast is not positioned centrally on the detector since the axillary muscle region and the arm base always cover the lateral region of the X-ray detector. Consequently, in MLO recordings the detector coverage as a result of the object is always greatly asymmetrical. This can result in portions of the tissue situated in the image recording region, that is to say in particular in the interspace between the compression plate and the X-ray detector, that are cut off in the individual projection images, particularly with regard to the axillary muscle region that is normally to be concomitantly recorded and diagnosed. This can lead to artifacts that reduce the image quality.

SUMMARY OF THE INVENTION

Therefore, the invention is based on the object of specifying a possibility for recording the underlying projection images which allows a better image quality of the tomosynthesis data set.

In order to achieve this object, in the case of a method of the type mentioned in the introduction, according to the invention it is provided that a recording angle interval that is asymmetrical relative to the central position is used in the case of an asymmetrically positioned breast, in particular for an MLO view.

It has been recognized that an asymmetrical, in particular the mediolateral oblique (MLO), positioning of the breast between the compression plate and the X-ray detector has the effect that the interspace between the X-ray detector and the compression plate, in a sectional plane in which the movement of the X-ray source also takes place, hence which contains the movement trajectory thereof, is filled with tissue asymmetrically since the breast (and, if appropriate, the axillary muscle that normally is to be concomitantly recorded in part in this case) projects into the interspace from one side. If the fan-shaped radiation field emerging from the X-ray source is then considered, it is evident that if the X-ray source is moved to the side opposite the side from which the breast projects, an increasing proportion of the projecting tissue situated between the compression plate and the X-ray detector is no longer detected, while a region of the interspace that is not filled with tissue is exposed to the radiation. However, if projection angles lying on the side from which the breast projects into the interspace are adopted, a significantly greater proportion of the tissue, that is to say in particular of the breast and, if appropriate, of the axillary muscle, is detected; however, a smaller proportion of the radiation affects the region free of tissue on account of the asymmetry on the opposite side.

In other words, this means that in the context of the present invention, preferably, on the side in the plane of the movement of the X-ray source from which the breast projects into the interspace between the compression plate and the X-ray detector, a larger angular distance of the outermost projection angle of the recording angle interval with respect to the central position is chosen compared with on the opposite side. In this regard, by use of the projection images, the largest possible proportion of the tissue situated in the interspace is also actually detected, which improves the database in the projection images and thus enables higher-quality tomosynthesis data sets that are freer of artifacts. The scanning process for recording the projection images is therefore carried out in a recording angle interval that is asymmetrical with respect to the center of the detector. If the central position therefore corresponds to a projection angle of 0°, a recording angle interval of −15° to +35° can be chosen for example instead of a recording angle interval of −25° to +25°, as used presently. In specific terms this means that, in the case of an MLO recording of the right breast, projection images on the right-hand side of the central position are recorded over a larger angular range compared with on the left-hand side, while the opposite holds true for the left breast projecting into the interspace from the other side. Generally, it can also be stated that the greater proportion of the recording angle interval lies on the axillary side.

This targeted asymmetry, which, of course, must vary within the limits of the basic angle interval, thus enables a significant improvement in the image quality of the tomosynthesis. The regions of undetected tissue in the respective outer projection images, that is to say the edge projection angles of the recording angle interval, are reduced, which also holds true for an overall consideration of the recorded projection images. Fewer artifacts are generated in this way. Overall, it can be stated that a further degree of freedom is used to optimize breast tomosynthesis preferably in MLO projection. This marks a departure from the procedure—practiced exclusively hitherto—of using only intervals which extend symmetrically around the central position.

In a specific, simple configuration of the invention, it can be provided that an absolute value of the recording angle interval is predefined, which interval is displaced by a defined and/or determined displacement value. Consequently, a recording interval having a specific length, for example of 50°, and extending symmetrically around the central position can be taken as a basis, which interval is then displaced toward the side from which the breast projects into the interspace between the compression plate and the X-ray detector. In this case, the length, that is to say the absolute value, of the recording angle interval can be fixedly predefined, for example in the range of 15° to 60°, but it can also be predefined depending on the size of the breast to be recorded. This breast size can be derived for example from a prior recording by the X-ray device, for example the so-called two-dimensional pre-shot, such that a default extent of the recording angle interval of 50° down to 45° can be taken as a basis for example in the case of a relatively small breast.

If the displacement value is defined, it can be in the range of 10° to 15°, for example. It is preferred, however, to be able to carry out an individual adaptation to the current patient that goes beyond the adaptation of the extent of the recording angle interval, such that the displacement value, too, can be determined in particular from a prior recording, for example the pre-shot already mentioned.

Stated in general terms, one particularly preferred configuration of the present invention therefore provides that, before the recording of the projection images with the breast already positioned, a two-dimensional prior recording is recorded by the X-ray device, which is evaluated for at least partly determining the recording angle interval. Such prior recordings are already known as a pre-shot and can be recorded automatically, for example by a control device of the X-ray device, in order to enable an automatic, patient-specific setting of the recording trajectory, here specifically of the recording angle interval. Low-dose prior recordings are involved here, in particular.

In this case, one development provides that the recording angle interval is determined depending on an asymmetry variable determined from the prior recording and describing the asymmetrical distribution of the tissue in the interspace between the compression plate and the X-ray detector, and/or depending on a breast size determined from the prior recording. By way of example, it is possible to determine what percentage of the tissue situated overall within the interspace between the compression plate and the X-ray detector is situated in that half of the interspace from which the breast projects in the interspace. It is analogously possible to determine the proportion in which no tissue is present. The more tissue is situated on the projecting side, the larger, for example, a defined displacement of the recording angle interval can be chosen to be proceeding from a symmetrical arrangement thereof. By way of example, if 70% of the tissue is situated in the half of the projecting side, a displacement value of 10° can be chosen, and a correspondingly greater displacement value can be chosen for greater proportions. In developments, the breast size per se can also have an influence as a parameter. It should also be pointed out that it is conceivable to consider the greatest possible extent of the breast within the interspace over the length, but proportions can also be determined from a combination/summation from a plurality of parallel planes. Besides the possibilities already mentioned for the asymmetry variable, that is to say a proportion of the tissue lying in one half of the interspace and/or a tissue-free proportion of the interspace, a further suitable parameter which can be taken into account when specifically determining the recording angle interval, in particular the displacement thereof from a symmetrical recording angle interval, is also the size of the breast which is intended to be recorded.

In this context, however, one particularly advantageous configuration provides that a first outermost projection angle of the recording angle interval at which a projection image is recorded, on the side from which the breast projects into the interspace between the compression plate and the X-ray detector, is determined such that an outer ray of the radiation field emitted by the X-ray source impinges on the corresponding outer edge of the detection area of the detector in a manner touching the breast at the edge. Since the radiation field of the detector is known, the geometrical shape thereof can be used to determine an ideal outermost position of the X-ray source, that is to say an outermost projection angle which bounds the recording angle interval, on the side from which the breast projects. A maximum benefit of the X-ray radiation occurs if even the X-ray situated furthest away from the projecting side firstly also affects tissue, but secondly can be measured, hence impinges on the active detection area. Consequently, it is possible to determine a projection angle at which this case occurs and which thus allows the recording of a maximum amount of tissue, without new artifacts occurring as a result of portions of tissue cut off on the side opposite the projecting side.

Once a delimitation of the recording angle interval in this way is known, one expedient development provides that in the case of an extent—which is predefined, in particular also automatically on the basis of the prior recording—of the recording angle interval, that is to say in the case of a predefined absolute value of the recording angle interval, the second outermost projection angle of the recording angle interval is determined from the predefined length and the first outermost projection angle. In this case, as already mentioned, it is particularly advantageous if the extent of the recording angle interval results from the breast size, wherein it goes without saying that further parameters can also be taken into account. In this way, overall, a patient-specific choice—possible in a fully automated manner—of an optimum recording angle interval for an MLO positioning is possible.

It is preferred, moreover, if a collimator of the X-ray source is set automatically depending on a tissue distribution on the X-ray detector determined from the prior recording such that the radiation field of the X-ray source is restricted to tissue-containing parts of the interspace between the compression plate and the X-ray detector. On account of the asymmetrical distribution of the tissue in the interspace, in the case of an automatically drivable collimator it is also possible to realize an asymmetrical insertion for the radiation field, with the result that the dose burden, in particular owing to scattered radiation, for the patient can be significantly reduced. Since the tissue distribution in the interspace is preferably determined with regard to the determination of the recording interval anyway, it is therefore known, together with the geometrical properties of the radiation field of the X-ray source, which rays would pass through tissue and which would not. The rays of the radiation field which would not pass through tissue and would thus ultimately impinge on the X-ray detector without having been used can be shielded with the aid of the collimator. In this regard, an optimization of the patient's dose is also possible.

A further possibility for optimization with regard to the X-ray dose arises in one advantageous configuration of the present invention in which at least partly different X-ray doses are used for the recording of the projection images depending on the projection angle of the recording angle interval. That means that the X-ray dose is distributed non-uniformly among the individual projection images, wherein a higher X-ray dose is expediently applied for the larger angles on the projecting-side proportion of the recording interval since longer tissue paths are then covered. In general terms, it can therefore be stated that the X-ray dose can be chosen depending on an expected tissue length traversed by the X-rays.

The tissue lengths can particularly advantageously be determined from the image data of the prior recording, such as has already been described above as pre-shot. Specifically, provision can be made here for the tissue length to be determined on the basis of a segmentation and/or a measure of the tissue density as determined from the gray-scale values of the prior recording. Corresponding possibilities for segmentation not only of the tissue itself, that is to say in particular of the thoracic wall, but also for example of the region in which axillary tissue is also present are already known. Precisely in regions in which the X-ray radiation has to penetrate not only through tissue of the breast but also through tissue of the axillary muscle, it is more expedient to set higher X-ray doses. An estimation regarding tissue lengths and, in particular, the density of the tissue is provided by the gray-scale values in the two-dimensional prior recording, which can be compared for example for different zones in order to obtain a measure of the density and hence corresponding absorption lengths. Model assumptions about the structure of the breast and the like can also influence such estimations of tissue lengths or absorption lengths.

It is conceivable to use a compression plate that is displaceable parallel to the X-ray detector in the context of the invention for further advantages with regard to imaging.

It can be expedient for such a compression plate embodied in a displaceable fashion to be displaced toward the X-ray detector to the side from which the breast projects into the interspace between the compression plate and the X-ray detector. Even if only relatively small displacements will normally be possible in this case, nevertheless an adaptation is effected with regard to the extended, asymmetrical recording geometry, which further benefits the image quality.

It should additionally be noted at this juncture that, of course, other possibilities for improving the recording geometry at larger projection angles can also be employed in the context of the present invention. By way of example, detectors had been proposed in which the breast rests on an X-ray detector housing of the X-ray detector, while the actual detection area is mounted pivotably in the interior of the housing and can thus be rotated at least slightly with the pivoting of the X-ray source in order to prevent X-ray radiation from impinging too obliquely on the detection area. Such techniques can of course also be used in the context of the present invention.

It is preferred if, during the recording of the projection images, the projection angle of the recording angle interval deviating from the central position by the largest absolute value is moved to first, wherein during the movement process a synchronization process between the X-ray detector and the X-ray source is carried out. As a result of the longer movement path there is ultimately more time until the corresponding outermost projection angle (using the terminology above the first outermost projection angle) is reached, and so there is also more time available for concluding the synchronization of X-ray source and X-ray detector. In this case, in particular, the X-ray detector can form a "Master" that can signal its readiness to the X-ray source.

Besides the method, the invention also relates to an X-ray device for recording a tomosynthesis data set of a breast of a patient, comprising an X-ray detector for the support of the breast, a compression plate for the breast, the compression plate being parallel to the X-ray detector, an X-ray source, which is movable in a basic angle interval around a central position, in which the midperpendicular of the detector area corresponds to the central ray of the X-ray source, for the purpose of recording projection images at different projection angles into different angular positions, and a control device designed for carrying out the method according to the invention. All explanations regarding the method according to the invention can be analogously applied to the X-ray device according to the invention, such that the advantages already mentioned can be achieved with said X-ray device, too.

The present invention can also be realized as a computer program if the corresponding recording processes are regarded as corresponding drive processes for the various components of the X-ray device within the computer program.

Other features which are considered as characteristic for the invention are set forth in the appended claims.

Although the invention is illustrated and described herein as embodied in a method for recording a tomosynthesis data set with an X-ray device, and an X-ray device it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 6 is a flowchart for illustrating a method according to the invention.

DETAILED DESCRIPTION OF THE INVENTION

Figure 1:
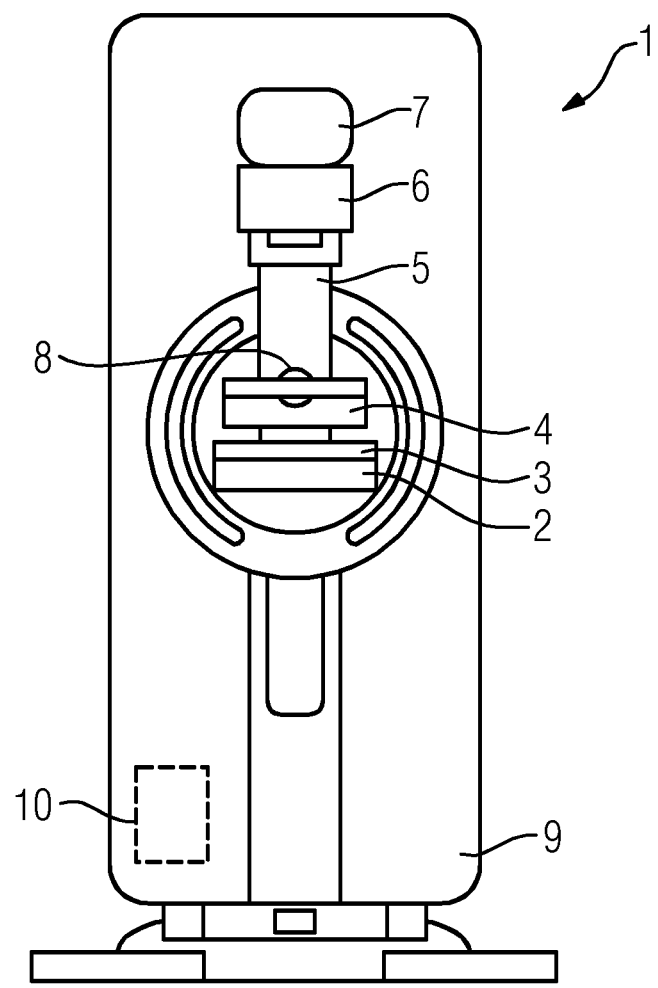
FIG. 1 is a basic schematic diagram of an X-ray device according to the invention for tomosynthesis imaging of a female breast.

Referring now to the figures of the drawings in detail and first, particularly to FIG. 1 thereof, there is shown a basic schematic diagram of an X-ray device 1 according to the invention in a basic schematic diagram of a front view. Such an X-ray device can also be referred to as a tomosynthesis device or mammography device. The X-ray device 1 contains an object table 2, on which an X-ray detector 3 is arranged, onto which a patient's breast to be recorded can be placed. By means of a compression plate 4 running parallel to the X-ray detector 3, the compression plate 4 being movable in a vertical direction in the setting in FIG. 1, it is possible to compress the breast in an interspace between the X-ray detector 3 and the compression plate 4. In this case, the compression plate 4 is arranged displaceably on a holding arm 5, which also carries the object table 2 and the X-ray source 6, which, relative to the mount 5, by a suitable movement device 7, can be brought into different angular positions (projection angles) with respect to the X-ray detector 3, which is non-movable here relative to the mount 5.

The entire recording arrangement formed by the X-ray detector 3, the X-ray source 6 and the compression plate 4 is in turn mounted pivotably by a pivoting device 8, such that ultimately the holding arm 5 and with it the X-ray detector 3 can be tilted, but the possible relative alignments of the X-ray detector 3 and of the X-ray source 6 are maintained in this case.

The components shown are in turn carried by a stand 9, in which, merely indicated here, a control device 10 of the X-ray device 1 can also be arranged, which is designed for carrying out the method according to the invention. It goes without saying that configurations are also conceivable in which an operating terminal (not shown more specifically here) belongs to the X-ray device 1 and can also comprise the control device 10, but at least contains an operating device and/or a display device for an operator.

FIG. 1 shows the recording arrangement in a position such as is used for tomosynthesis data sets in the CC view (Cranial-Caudal view), wherein the breast is positioned centrally on the X-ray detector 3. The X-ray source 6 and the X-ray detector 3 are shown in their arrangement with respect to one another in a basic position in which the direction of the central ray of the X-ray source 6 corresponds to the midperpendicular of the X-ray detector 3; proceeding from this central position, it is possible to move the X-ray source 6, as already mentioned, for recording projection images at different projection angles within a basic angle interval, defined by the mechanical restrictions, into different angular positions.

If the intention is to record tomosynthesis data sets of the breast in a mediolateral oblique view (MLO view), the recording arrangement, by the pivoting device 8, as already mentioned, is brought into a tilted position in which, for example, the X-ray detector 3 adopts an angle of 45° relative to the vertical.

Figure 2:
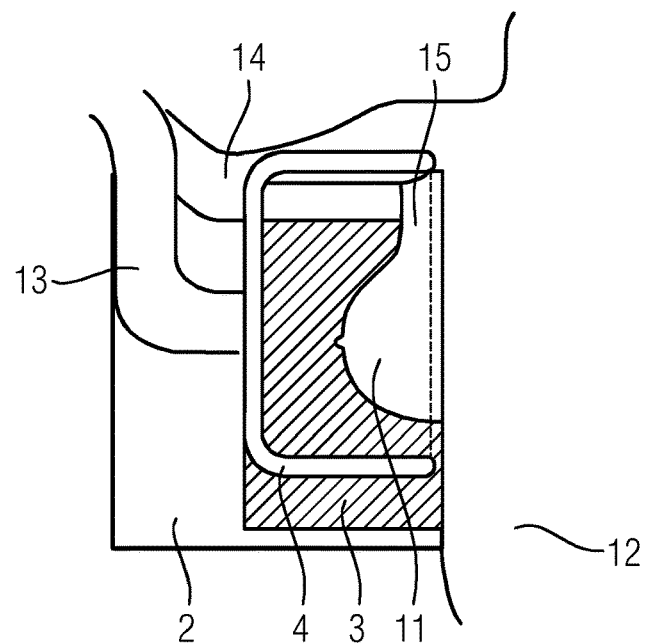
FIG. 2 is a schematic diagram for elucidating a positioning of the breast for an MLO view.

The corresponding situation is indicated by the basic schematic diagram in FIG. 2, wherein for the sake of simplicity the compression plate 4 is also illustrated as light-transmissive in the optical region, apart from its border. FIG. 2 reveals the inclined X-ray detector 3 on the object table 2, above which the compression plate 4 is situated, in a manner forming an interspace for a breast 11 of a patient 12, the compression plate being mounted on an arm 13 in a displaceable manner perpendicular to the detector area in the present case. The breast 11 is placed on the X-ray detector 3 and is compressed by the compression plate 4, while the arm 14 of the patient 12 rests on the X-ray detector 3 or object table 2, as a result of which a certain proportion 15 of the axillary muscle is also located in the interspace between the X-ray detector 3 and the compression plate 4, hence in the imaging region.

Figure 3:
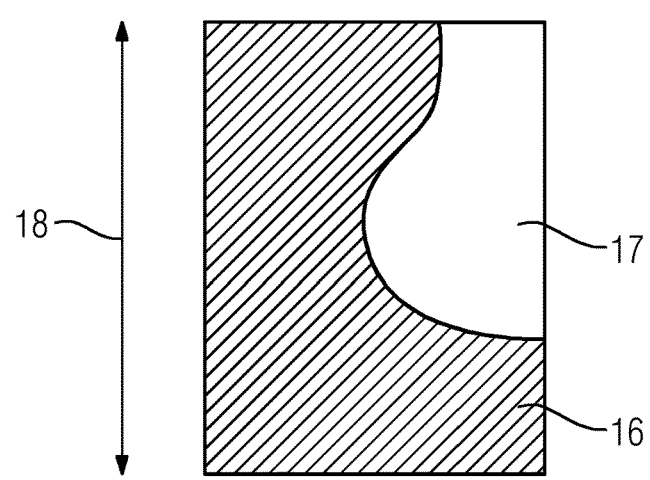
FIG. 3 is an illustration showing the position of the breast in accordance with FIG. 2 in a plan view of the detector.

An arrangement of an arm 14 and breast 11 for the MLO recording causes an asymmetrical distribution of a tissue 17 (of the breast 11 and of the proportion 15) on the detection area 16 also in the direction 18, as is shown in FIG. 3, wherein the direction 18 corresponds to the possibility for movement of the X-ray source 6 relative to the X-ray detector 3.

Figure 4:
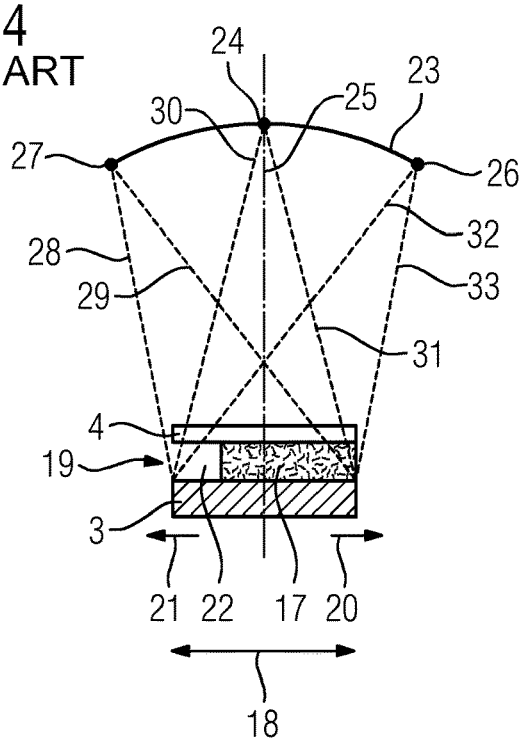
FIG. 4 is a sectional view in the plane of the movement of an X-ray source for a recording path in accordance with the prior art.

This will be explained in greater detail with reference to FIG. 4 which shows a tomosynthesis recording process for projection images in the case of an MLO positioning of a breast 11 in accordance with the prior art. The figure firstly shows an interspace 19 between the X-ray detector 3 and the compression plate 4, in which interspace the tissue 17 is situated in an asymmetrical distribution relative here to a region of greater extent of the tissue 17 that is located on the right in FIG. 3, the tissue filling the interspace 19 from a side 20 from which the breast 11 projects into the interspace 19, and leaving a free space 22 on the opposite side 21.

A shown movement path 23 (recording trajectory) of the X-ray source 6 corresponds to the recording process in the prior art, in which the recording angle interval (and hence also the movement path 23) containing the projection angles at which projection images are recorded extends symmetrically around a central position 24, wherein a midperpendicular 25 of the X-ray detector 3 corresponding to the central ray of the X-ray source 6 in the central position 24 is shown.

The movement path 23 and hence the recording angle interval are bounded by outermost positions 26, 27 situated symmetrically with respect to the central position 24. The outermost positions clearly corresponding to outermost projection angles at which a projection image is intended to be recorded. By way of example, if an absolute value of the recording angle interval of 50° is intended to be covered and if the central position 24, as known in principle, corresponds to a projection angle of 0°, the outermost positions 26, 27 can correspond to +25° and −25°, for example.

In addition, the extents of the radiation field that impinges on the detection area 16 of the X-ray detector 3 are shown by respective outer boundaries 28 to 33.

With regard to the outermost position 27, a boundary 29 reveals that a part of the tissue 17, in particular in the region of the proportion 15 of the axillary muscle, is no longer covered by X-ray radiation, while, also see boundary 28, the free space 22 is covered by X-ray radiation, which, however, does not yield any desired or useful image information. The fact that a part of the tissue 17 is not contained in some projection images means, however, that artifacts can occur.

The boundaries 32 and 33 of the other outermost position 26 show, however, that a complete coverage of the tissue 17 is provided here.

Therefore, the invention proposes, as is also illustrated with reference to FIG. 5, choosing an asymmetrical recording angle interval with respect to the central position 24 and hence also an asymmetrical movement path 34 of the X-ray source 6. In this case, the larger proportion of the movement path 34 is situated toward the side 20 from which the breast 11 projects into the interspace 19. The new outermost position 35 thus clearly corresponds to a larger positive projection angle, for example a projection angle displaced by 10 to 15° from the previous outermost projection angle; the new outermost position 36 is closer to the central position 24.

For clarification purposes, boundaries 37 to 40 are shown again at least for the outermost positions 35, 36, wherein a significantly smaller proportion of the tissue 17 above the detection area 16 of the X-ray detector 3 is cut off by the boundary 38 than by the boundary 29.

The boundary 39 already indicates how an outermost projection angle assigned to the outermost position 35 can be determined. The boundary 39 of the radiation field which would be emitted from the outermost position 35 ultimately corresponds to the outermost ray that would still impinge on the X-ray detector 3, more precisely the detection area 16 thereof. Clearly the ray also exactly touches the upper boundary of the tissue 17 in the interspace toward the side 21, such that the outermost position 35 is thus chosen such that the entire tissue 17 is detected, without cut-off parts then occurring on the other side, that is to say the side 21. In this case, the boundary 39 (and hence the outermost position 35) can be determined from a prior recording, a so-called pre-shot, that is to say a two-dimensional X-ray image which is recorded with the breast 11 already having been positioned in the central position 24. From the pre-shot, by means of segmentation it is possible to draw a conclusion about the distribution of the tissue 17 in the interspace 19. The geometry of the radiation field emitted by the X-ray source 6 is already known. Consequently, the boundary 39 can be determined, wherein, of course, mechanical restrictions of the movability of the X-ray source 6 should be taken into consideration; consequently, an outermost projection angle determined in this way should not lie outside the basic angle interval. However, other possibilities are also conceivable for defining the outermost positions 35, 36 or a displacement in the case of a fixed absolute value, that is to say fixed extent, of the recording angle interval, in particular depending on a present size of the breast 11.

Figure 5:
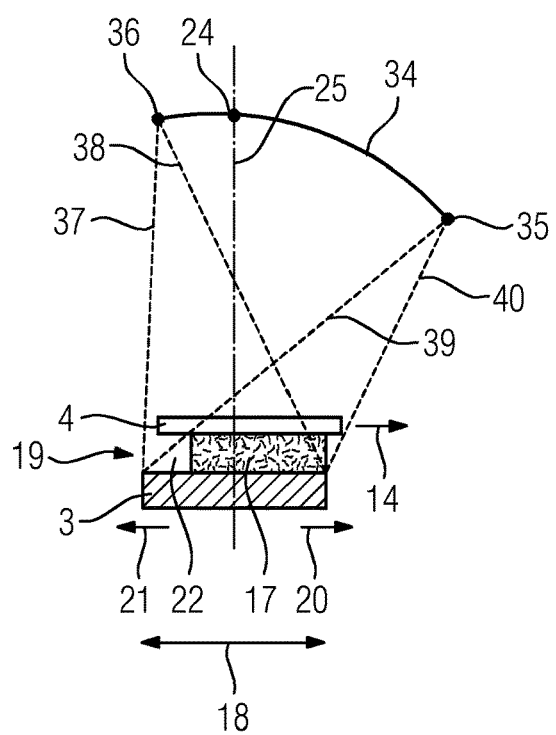
FIG. 5 is a sectional view of the plane in which the X-ray source is moved in the case of a recording path in accordance with the present invention.

FIG. 5 also already reveals a further configuration that is useful, namely the isplaceability of the compression plate 4 in the direction 18, which is displaced in the present case to the side 20, see arrow 41, from which the breast 11 projects into the interspace 19. As shown by the boundary 40, it is thus possible to avoid a situation, for example, in which information about tissue 17 to be reconstructed is concealed/supplemented with ray paths through relatively long tissue paths of the body of the patient 12.

FIG. 6 then shows a flowchart of one exemplary embodiment of the method according to the invention, wherein, in a step S1 after a positioning of the breast 11 for the recording of an MLO view, hence of an MLO tomosynthesis data set, a pre-shot is recorded as a prior recording in the central position 24, that is to say at a projection angle of 0°.

In a step S2, the prior recording is then evaluated in order to determine a suitable recording angle interval and further recording parameters, in which case, of course, further information concerning the specific patient 12 can also have an influence. Firstly, the extent, that is to say the absolute value, of the recording angle interval is determined depending on the size of the breast 11 to be recorded, which can easily be determined from the prior recording. By way of example, for larger breasts 11 it is possible to choose a longer recording angle interval than for smaller breasts, particularly in the range of 30° to 50°.

This is followed by determining the outermost projection angle of the recording angle interval on a side 20, hence the side from which the breast 11 projects into the interspace 19. This is carried out as described with reference to FIG. 5. From the extent of the recording angle interval as determined previously, after all, the second outermost projection angle of the recording angle interval can then likewise be determined easily. It goes without saying that alternative variations are also conceivable for defining the recording angle interval. In one alternative variant, by way of example, it is possible to determine a proportion of the tissue 17 which lies in that half of the interspace 19 which is assigned to the side 20, wherein different regions of the proportion are assigned different displacement values by which the recording angle interval is to be displaced from a symmetrical position around the central position 24. The displacement values can be in the range of 10° to 15°, for example.

Further recording parameters are also determined in step S2. In this regard, from the distribution of the tissue 17 above the detector area 16, that is to say in the interspace 19, which distribution can be determined from the prior recording, it is possible to derive what tissue lengths or absorption lengths X-rays have to penetrate through in order to impinge on the detection area 16. Correspondingly, a different X-ray dose can be chosen for different projection angles. These different doses can be taken into account, of course, in the reconstruction of the tomosynthesis data set from the projection images. Furthermore, from the known distribution of the tissue 17 in the interspace 19, collimator settings for a drivable collimator arranged in front of the X-ray source 6 are determined by automatic evaluation just like the other recording parameters described here. In this way, it is possible to avoid a situation in which too much X-ray radiation passes into the free space 22 and possibly generates scattered radiation there.

Once all the recording parameters have been determined in step S2, in a step S3 the X-ray source 6 is moved into a starting position by means of the movement device 7, the starting position corresponding in the present case to the outermost position 35 further away from the central position 24. During the time in which the X-ray source 6 is moved, the synchronization of the X-ray source 6 with the X-ray detector 3 is carried out, for which a longer time is thus available.

In a step S4, the recording parameters are then used to record projection images at different projection angles, while the X-ray source is moved along the movement path 34 that is asymmetrical with respect to the central position 24. In a step S5, finally, the tomosynthesis data set can be reconstructed from the projection images.

Although the invention has been more specifically illustrated and described in detail by means of the preferred exemplary embodiment, nevertheless the invention is not restricted by the examples disclosed and other variations can be derived therefrom by the person skilled in the art, without departing from the scope of protection of the invention.

The following is a summary list of reference numerals and the corresponding structure used in the above description of the invention:
1 X-ray device
2 Object table
3 X-ray detector
4 Compression plate
5 Mount
6 X-ray source
7 Movement device
8 Pivoting device
9 Stand
10 Control device
11 Breast
12 Patient
13 Arm
14 Arm
15 Proportion
16 Detection area
17 Tissue
18 Direction
19 Interspace
20 Side
21 Side
23 Free space
24 Central position
25 Midperpendicular
26 Position
27 Position
28 Boundary
29 Boundary
30 Boundary
31 Boundary
32 Boundary
33 Boundary
34 Movement path
35 Position
36 Position
37 Boundary
38 Boundary
39 Boundary
40 Boundary
41 Arrow

The invention claimed is:

1. A method for recording a tomosynthesis data set of a breast of a patient with an X-ray device having an X-ray detector for supporting the breast, a compression plate for the breast, the compression plate being disposed parallel to the X-ray detector, and an X-ray source being movable in a basic angle interval around a central position, in which a mid-perpendicular of a detector area corresponds to a central ray of the X-ray source, for recording projection images at different projection angles into different angular positions, which comprises the steps of:
reconstructing the tomosynthesis data set from the projection images recorded at the different projection angles over a recording interval; and
using a recording angle interval being asymmetrical relative to the central position in a case of an asymmetrically positioned breast, in that on a side in a plane of a movement of the X-ray source from which the breast projects into an interspace between the compression plate and the X-ray detector, a larger angular distance of an outermost projection angle of the recording angle interval with respect to the central position is chosen compared with on an opposite side, such that the greater proportion of the recording angle interval lies on the axillary side.

2. The method according to claim 1, which further comprises predefining an absolute value of the recording angle interval, the recording angle interval is displaced by a defined and/or determined displacement value.

3. The method according to claim 2, wherein a predefinition of the absolute value of the recording angle interval is carried out depending on a size of the breast determined from at least one prior recording of the X-ray device, and/or in that the defined displacement value is in a range of 10° to 15°.

4. The method according to claim 1, wherein before recording of the projection images with the breast already positioned, recording a two-dimensional prior recording by the X-ray device, the two-dimensional prior recording is evaluated for at least partly determining the recording angle interval.

5. The method according to claimed in claim 4, which further comprises determining the recording angle interval depending on an asymmetry variable determined from the two-dimensional prior recording and describing an asymmetrical distribution of a tissue in the interspace between the compression plate and the X-ray detector, and/or depending on a breast size determined from the two-dimensional prior recording.

6. The method according to claim 5, wherein a proportion of the tissue lying in one half of the interspace and/or a tissue-free proportion of the interspace are/is used as the asymmetry variable.

7. The method according to claim 4, which further comprises determining a first outermost projection angle of the recording angle interval at which a projection image is recorded, on the side from which the breast projects into the interspace between the compression plate and the X-ray detector, such that an outer ray of a radiation field emitted by the X-ray source impinges on a corresponding outer edge region of the detection area of the X-ray detector in a manner touching the breast at an edge.

8. The method according to claim 7, wherein in a case of a predefined absolute value of the recording angle interval, determining a second outermost projection angle of the recording angle interval from a length and the first outermost projection angle.

9. The method according to claim 4, which further comprises setting a collimator of the X-ray source automatically depending on a tissue distribution determined from the two-dimensional prior recording such that a radiation field of the X-ray source is restricted to tissue-containing parts of the interspace between the compression plate and the X-ray detector.

10. A method for recording a tomosynthesis data set of a breast of a patient with an X-ray device having an X-ray detector for supporting the breast, a compression plate for the breast, the compression plate being disposed parallel to the X-ray detector, and an X-ray source being movable in a basic angle interval around a central position, in which a mid-perpendicular of a detector area corresponds to a central ray of the X-ray source, for recording projection images at different projection angles into different angular positions, which comprises the steps of:
- reconstructing the tomosynthesis data set from the projection images recorded at the different projection angles over a recording interval;
- using a recording angle interval being asymmetrical relative to the central position in a case of an asymmetrically positioned breast, in that on a side in a plane of a movement of the X-ray source from which the breast projects into an interspace between the compression plate and the X-ray detector, a larger angular distance of an outermost projection angle of the recording angle interval with respect to the central position is chosen compared with on an opposite side;
- wherein before recording of the projection images with the breast already positioned, recording a two-dimensional prior recording by the X-ray device, the two-dimensional prior recording being evaluated for at least partly determining the recording angle interval;
- determining the recording angle interval depending on an asymmetry variable determined from the two-dimensional prior recording and describing an asymmetrical distribution of a tissue in the interspace between the compression plate and the X-ray detector, and/or depending on a breast size determined from the two-dimensional prior recording; and
- using at least partly different X-ray doses for the recording of the projection images depending on a projection angle of the recording angle interval.

11. The method according to claim 10, wherein when recording the two-dimensional prior recording, choosing an X-ray dose depending on an expected tissue length traversed by X-rays.

12. The method according to claim 11, which further comprises determining a tissue length on a basis of a segmentation and/or a measure of a tissue density as determined from gray-scale values of the two-dimensional prior recording.

13. The method according to claim 1, wherein in a case where the compression plate is embodied such that the compression plate is displaceable parallel to the X-ray detector, the compression plate is displaced toward the X-ray detector to the side from which the breast projects into the interspace between the compression plate and the X-ray detector.

14. The method according to claim 1, wherein for recording the projection images, a projection angle deviating from the central position by a largest absolute value is moved to first, wherein during a movement process a synchronization process between the X-ray detector and the X-ray source is carried out.

15. An X-ray device for recording a tomosynthesis data set of a breast of a patient, the X-ray device comprising:
- an X-ray detector for supporting the breast;
- a compression plate for the breast, said compression plate being disposed parallel to said X-ray detector;
- an X-ray source being movable in a basic angle interval around a central position, in which a mid-perpendicular of a detector area corresponds to a central ray of said X-ray source, for recording projection images at different projection angles into different angular positions; and
- a control device configured to carry out the method according to claim 1.

* * * * *